(12) United States Patent
Claude

(10) Patent No.: US 7,261,946 B2
(45) Date of Patent: Aug. 28, 2007

(54) BLOCK COPOLYMERS OF ACRYLATES AND METHACRYLATES WITH FLUOROALKENES

(75) Inventor: Charles D. Claude, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 287 days.

(21) Appl. No.: 10/714,111

(22) Filed: Nov. 14, 2003

(65) Prior Publication Data

US 2005/0107531 A1    May 19, 2005

(51) Int. Cl.
*A61L 31/10* (2006.01)

(52) U.S. Cl. ............... 428/500; 428/523; 623/1.1; 623/1.42

(58) Field of Classification Search ............. 623/1.1, 623/1.42, 1.15; 424/423
See application file for complete search history.

(56) References Cited

U.S. PATENT DOCUMENTS

| | | | |
|---|---|---|---|
| 4,158,678 A | 6/1979 | Tatemoto et al. | |
| 4,412,054 A * | 10/1983 | Yamabe et al. | 528/70 |
| 4,501,869 A | 2/1985 | Tatemoto et al. | |
| 4,733,665 A | 3/1988 | Palmaz | 128/343 |
| 4,800,882 A | 1/1989 | Gianturco | 128/343 |
| 4,886,062 A | 12/1989 | Wiktor | 128/343 |
| 4,931,287 A | 6/1990 | Bae et al. | 424/484 |
| 4,977,901 A | 12/1990 | Ofstead | 128/772 |
| 5,019,096 A | 5/1991 | Fox, Jr. et al. | 623/1 |
| 5,112,457 A | 5/1992 | Marchant | 204/165 |
| 5,163,952 A | 11/1992 | Froix | 623/1 |
| 5,219,662 A * | 6/1993 | Grimminger et al. | 428/423.1 |
| 5,258,020 A | 11/1993 | Froix | 623/1 |
| 5,328,471 A | 7/1994 | Slepian | 604/101 |
| 5,455,040 A | 10/1995 | Marchant | 424/426 |
| 5,464,650 A | 11/1995 | Berg et al. | 427/2.3 |
| 5,578,073 A | 11/1996 | Haimovich et al. | 623/1 |
| 5,584,877 A | 12/1996 | Miyake et al. | 623/1 |
| 5,605,696 A | 2/1997 | Eury et al. | 424/423 |
| 5,607,467 A | 3/1997 | Froix | 623/1 |
| 5,616,338 A | 4/1997 | Fox, Jr. et al. | 424/423 |
| 5,667,767 A | 9/1997 | Greff et al. | 424/9.411 |
| 5,670,558 A | 9/1997 | Onishi et al. | 523/112 |
| 5,674,242 A | 10/1997 | Phan et al. | 606/198 |
| 5,700,286 A | 12/1997 | Tartaglia et al. | 623/1 |
| 5,716,981 A | 2/1998 | Hunter et al. | 514/449 |
| 5,723,219 A | 3/1998 | Kolluri et al. | 428/411.1 |
| 5,759,205 A | 6/1998 | Valentini | 623/16 |
| 5,824,049 A | 10/1998 | Ragheb et al. | 623/1 |
| 5,830,178 A | 11/1998 | Jones et al. | 604/49 |
| 5,837,313 A | 11/1998 | Ding et al. | 427/2.21 |
| 5,851,508 A | 12/1998 | Greff et al. | 424/9.411 |
| 5,858,746 A | 1/1999 | Hubbell et al. | 435/177 |
| 5,865,814 A | 2/1999 | Tuch | 604/265 |
| 5,873,904 A | 2/1999 | Ragheb et al. | 623/1 |
| 5,879,713 A | 3/1999 | Roth et al. | 424/489 |
| 5,932,299 A | 8/1999 | Katoot | 427/508 |
| 5,962,138 A | 10/1999 | Kolluri et al. | 428/411.1 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,015,541 A | 1/2000 | Greff et al. | 424/1.25 |
| 6,042,875 A | 3/2000 | Ding et al. | 427/2.24 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,143,354 A | 11/2000 | Koulik et al. | 427/2.24 |
| 6,153,252 A | 11/2000 | Hossainy et al. | 427/2.3 |
| 6,159,978 A | 12/2000 | Myers et al. | 514/252.1 |
| 6,165,212 A | 12/2000 | Dereume et al. | 623/1.13 |
| 6,177,523 B1 | 1/2001 | Reich et al. | 525/459 |
| 6,180,632 B1 | 1/2001 | Myers et al. | 514/252.1 |
| 6,214,901 B1 | 4/2001 | Chudzik et al. | 523/113 |
| 6,228,943 B1 | 5/2001 | Morikawa et al. | |
| 6,245,760 B1 | 6/2001 | He et al. | 514/234.8 |
| 6,248,129 B1 | 6/2001 | Froix | 623/1.42 |

(Continued)

FOREIGN PATENT DOCUMENTS

| | | | |
|---|---|---|---|
| EP | 0027028 | * | 4/1981 |
| EP | 0 291 297 | | 11/1988 |
| EP | 0 489 370 | | 6/1992 |
| EP | 0 665 023 | | 8/1995 |
| EP | 0 683 186 | | 11/1995 |
| EP | 0 924 257 | | 6/1999 |
| EP | 0 970 711 | | 1/2000 |
| EP | 1 023 879 | | 8/2000 |
| EP | 1 126 537 | | 8/2001 |
| EP | 1 192 957 | | 4/2002 |

(Continued)

OTHER PUBLICATIONS

Lewis, Richard J., Sr. (2002). Hawley's Condensed Chemical Dictionary (14th Edition). John Wiley & Sons, entry for "block polymer".*

(Continued)

*Primary Examiner*—Jeffre Mullis
(74) *Attorney, Agent, or Firm*—Squire, Sanders & Dempsey L.L.P.

(57) ABSTRACT

A block copolymer comprising a fluorinated block and a non-fluorinated block and method of making the block copolymer are provided. Also provided herein are a coating on an implantable device comprising the block copolymer and method of using the implantable device.

18 Claims, 1 Drawing Sheet

U.S. PATENT DOCUMENTS

| | | |
|---|---|---|
| 6,258,371 B1 | 7/2001 | Koulik et al. ............... 424/422 |
| 6,262,034 B1 | 7/2001 | Mathiowitz et al. .......... 514/44 |
| 6,270,788 B1 | 8/2001 | Koulik et al. ............... 424/423 |
| 6,277,449 B1 | 8/2001 | Kolluri et al. .............. 427/289 |
| 6,299,604 B1 | 10/2001 | Ragheb et al. .............. 604/265 |
| 6,306,176 B1 | 10/2001 | Whitbourne ............. 623/23.59 |
| 4,733,665 C2 | 1/2002 | Palmaz ...................... 606/108 |
| 6,344,035 B1 | 2/2002 | Chudzik et al. ............. 604/265 |
| 6,387,379 B1 | 5/2002 | Goldberg et al. ........... 424/400 |
| 6,482,834 B2 | 11/2002 | Spada et al. ................. 514/311 |
| 6,524,347 B1 | 2/2003 | Myers et al. ............. 514/252.1 |
| 6,528,526 B1 | 3/2003 | Myers et al. ............... 214/311 |
| 6,530,950 B1 | 3/2003 | Alvarado et al. .......... 623/1.13 |
| 6,530,951 B1 | 3/2003 | Bates et al. ................. 623/1.45 |
| 2001/0007083 A1 | 7/2001 | Roorda ...................... 623/1.15 |
| 2001/0014717 A1 | 8/2001 | Hossainy et al. ............. 525/60 |
| 2001/0020011 A1 | 9/2001 | Mathiowitz et al. .......... 514/44 |
| 2001/0029351 A1 | 10/2001 | Falotico et al. ........ 604/103.02 |
| 2001/0051608 A1 | 12/2001 | Mathiowitz et al. .......... 514/44 |
| 2002/0005206 A1 | 1/2002 | Falotico et al. ............. 128/898 |
| 2002/0007213 A1 | 1/2002 | Falotico et al. ............. 623/1.21 |
| 2002/0007214 A1 | 1/2002 | Falotico ..................... 623/1.21 |
| 2002/0007215 A1 | 1/2002 | Falotico et al. ............. 623/1.21 |
| 2002/0009604 A1 | 1/2002 | Zamora et al. ............. 428/450 |
| 2002/0016625 A1 | 2/2002 | Falotico et al. ............. 623/1.13 |
| 2002/0032414 A1 | 3/2002 | Ragheb et al. .............. 604/265 |
| 2002/0032434 A1 | 3/2002 | Chudzik et al. .......... 604/890.1 |
| 2002/0051730 A1 | 5/2002 | Bodnar et al. ................ 422/33 |
| 2002/0082679 A1 | 6/2002 | Sirhan et al. ............... 623/1.15 |
| 2002/0094440 A1 | 7/2002 | Llanos et al. ............... 428/421 |
| 2002/0111590 A1 | 8/2002 | Davila et al. ............... 604/265 |
| 2002/0123801 A1 | 9/2002 | Pacetti et al. ............. 623/1.46 |
| 2002/0165608 A1 | 11/2002 | Llanos et al. ............... 623/1.45 |
| 2002/0176849 A1 | 11/2002 | Slepian ...................... 424/93.7 |
| 2002/0188037 A1 | 12/2002 | Chudzik et al. ............. 523/112 |
| 2003/0004141 A1 | 1/2003 | Brown ....................... 514/152 |
| 2003/0028243 A1 | 2/2003 | Bates et al. ................. 623/1.15 |
| 2003/0028244 A1 | 2/2003 | Bates et al. ................. 623/1.15 |
| 2003/0031780 A1 | 2/2003 | Chudzik et al. .............. 427/2.1 |
| 2003/0036794 A1 | 2/2003 | Ragheb et al. .............. 623/1.15 |
| 2003/0039689 A1 | 2/2003 | Chen et al. .................. 424/468 |
| 2003/0040790 A1 | 2/2003 | Furst ......................... 623/1.11 |
| 2003/0060877 A1 | 3/2003 | Falotico et al. ............. 623/1.42 |
| 2003/0065377 A1 | 4/2003 | Davila et al. ............... 623/1.13 |
| 2003/0083646 A1 | 5/2003 | Sirhan et al. ............. 604/891.1 |
| 2003/0083739 A1 | 5/2003 | Cafferata ................... 623/1.42 |
| 2005/0107531 A1* | 5/2005 | Claude ........................ 525/88 |
| 2006/0134165 A1* | 6/2006 | Pacetti ....................... 424/422 |
| 2006/0173131 A1* | 8/2006 | Morikawa et al. .......... 525/102 |
| 2006/0235416 A1* | 10/2006 | Revis ........................... 606/74 |
| 2006/0282152 A1* | 12/2006 | Beyerlein et al. .......... 623/1.11 |
| 2007/0005092 A1* | 1/2007 | Godin et al. ................. 606/194 |

FOREIGN PATENT DOCUMENTS

| | | |
|---|---|---|
| EP | 1 231 239 | 8/2002 |
| JP | 59040066 | 3/1984 |
| WO | WO95/24929 | 9/1995 |
| WO | WO98/08463 | 3/1998 |
| WO | WO 00/12147 | 3/2000 |
| WO | WO 00/59963 | 10/2000 |
| WO | WO 00/64506 | 11/2000 |
| WO | WO 01/01890 | 1/2001 |

OTHER PUBLICATIONS

Invitation to pay additional fees for PCT/US2004/037474, filed Nov. 10, 2004, mailed Mar. 8, 2004, 8 pgs.
U.S. Appl. No. 10/176,504, filed Jun. 21, 2002, Roorda et al.
U.S. Appl. No. 10/176,510, filed Jun. 21, 2002, Hossainy et al.
U.S. Appl. No. 10/177,117, filed Jun. 21, 2002, Hossainy.
U.S. Appl. No. 10/177,154, filed Jun. 21, 2002, Hossainy et al.
U.S. Appl. No. 10/251,111, filed Sep. 19, 2002, Hossainy et al.
U.S. Appl. No. 10/320,899, filed Dec. 16, 2002 Shah et al.
U.S. Appl. No. 10/376,348, filed Feb. 26, 2003, Ding et al.
U.S. Appl. No. 10/428,691, filed May 1, 2003, Pacetti.
International Search Report and Written Opinion of International Application No. PCT/US2004/037474 filed Nov. 10, 2004, mailed Jun. 30, 2005, 16 pages.

* cited by examiner

BLOCK COPOLYMERS OF ACRYLATES AND METHACRYLATES WITH FLUOROALKENES

BACKGROUND OF THE INVENTION

1. Field of the Invention

This invention generally relates to fluorinated and non-fluorinated block copolymer and composition formed therefrom useful for coating an implantable device such as a drug eluting stent.

2. Description of the Background

Blood vessel occlusions are commonly treated by mechanically enhancing blood flow in the affected vessels, such as by employing a stent. Stents are used not only for mechanical intervention but also as vehicles for providing biological therapy. To effect a controlled delivery of an active agent in stent medication, the stent can be coated with a biocompatible polymeric coating. The biocompatible polymeric coating can function either as a permeable layer or a carrier to allow a controlled delivery of the agent.

Fluorinated polymers, such as poly(vinylidene fluoride-co-hexafluoropropylene), have been used to form drug-eluting stent (DES) coatings and can effectively control the release of pharmaceutical agents from a stent. DES coatings formed of these fluorinated polymers also have excellent mechanical properties and are biocompatible and biologically inert. However, polymers of fluorinated olefins are very hydrophobic and may have low glass transition temperatures. Too high a hydrophobicity of the polymeric coating on a DES often reduces the permeability of the coating and thus slows down the release rate of a drug on the coating to an undesirable level.

The polymer and methods of making the polymer disclosed herein address the above described problems.

SUMMARY OF THE INVENTION

Disclosed herein is a fluorinated block copolymer comprising a fluorinated block and a non-fluorinated block. The non-fluorinated block of the polymer provides improved vascular responses and/or improved permeability for controlled release of pharmaceutical agents.

In accordance with one aspect of the invention, the non-fluorinated block comprises a polyolefinic block of the following structure:

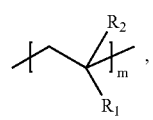

wherein $R_1$ is $-CH_3$, $-CF_3$, $-CH_2CH_3$, $-CH_2CH_2CH_3$, $-CH_2CH_2CH_2CH_3$, -phenyl, naphthyl, $-COOR_3$, or $-CONR_3R_4$;

wherein $R_2$ is $-H$, $-CH_3$, $-CF_3$, $-CH_2CH_3$, $-CH_2CH_2CH_3$, $-CH_2CH_2CH_2CH_3$, -phenyl, or naphthalenyl; and wherein $R_3$ and $R_4$ are $-CH_3$, $-CH_2CH_3$, $-CH_2CH_2CH_3$, $-CH_2CH_2CH_2CH_3$, $-CH_2CH_2OH$, or -PEG.

In another embodiment, the fluorinated block can be, for example, a block of poly(fluorinated olefins), for example, a block having the following structure:

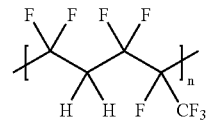

In a further embodiment, the fluorinated block copolymer has a structure as shown below:

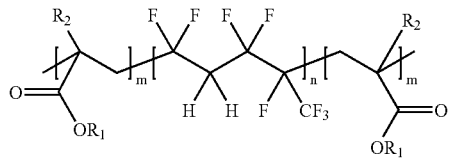

wherein $R_1$ is $-CH_3$, $-CH_2CH_3$, $-CH_2CH_2CH_3$, $-CH_2CH_2CH_2CH_3$, $-CH_2CH_2OH$, or -PEG; and wherein $R_2$ is $-H$, $-CH_3$, $-CF_3$, $-CH_2CH_3$, $-CH_2CH_2CH_3$, $-CH_2CH_2CH_2CH_3$, -phenyl, or naphthyl.

The polymer can form a coating composition for coating an implantable device and/or a coating formed thereof for controlling the release rate of a bioactive agent. The block copolymer can be formed by polymerizing a non-fluorinated olefin such as acrylate, methacrylate, or styrene in the presence of a copper catalyst, such as an ATRP (atom transfer radical polymerization) catalyst (see, for example, Matyjaszewski, K. *Controlled Radical Polymerization*; American Chemical Society: Washington, D.C., 1998; Vol. 685; Honigfort, M. E.; Brittain, W. J.; Bosanac, T.; Wilcox, C. S. *Polym. Prepr.* 2002, 43, 561), and a fluorinated di-halo macromer.

The fluorinated block copolymer can be used to form a coating composition comprising the fluorinated block copolymer alone or in combination with another material or polymer, optionally with a bioactive agent. The coating composition thus formed can be coated onto an implantable device such as a DES. The release rate of the bioactive agent on the DES can be controlled by fine-tuning the hydrophobicity of the fluorinated block copolymer using a hydrophilic group such as ethylene glycol or polyethylene glycol.

DETAILED DESCRIPTION

Figure 1:
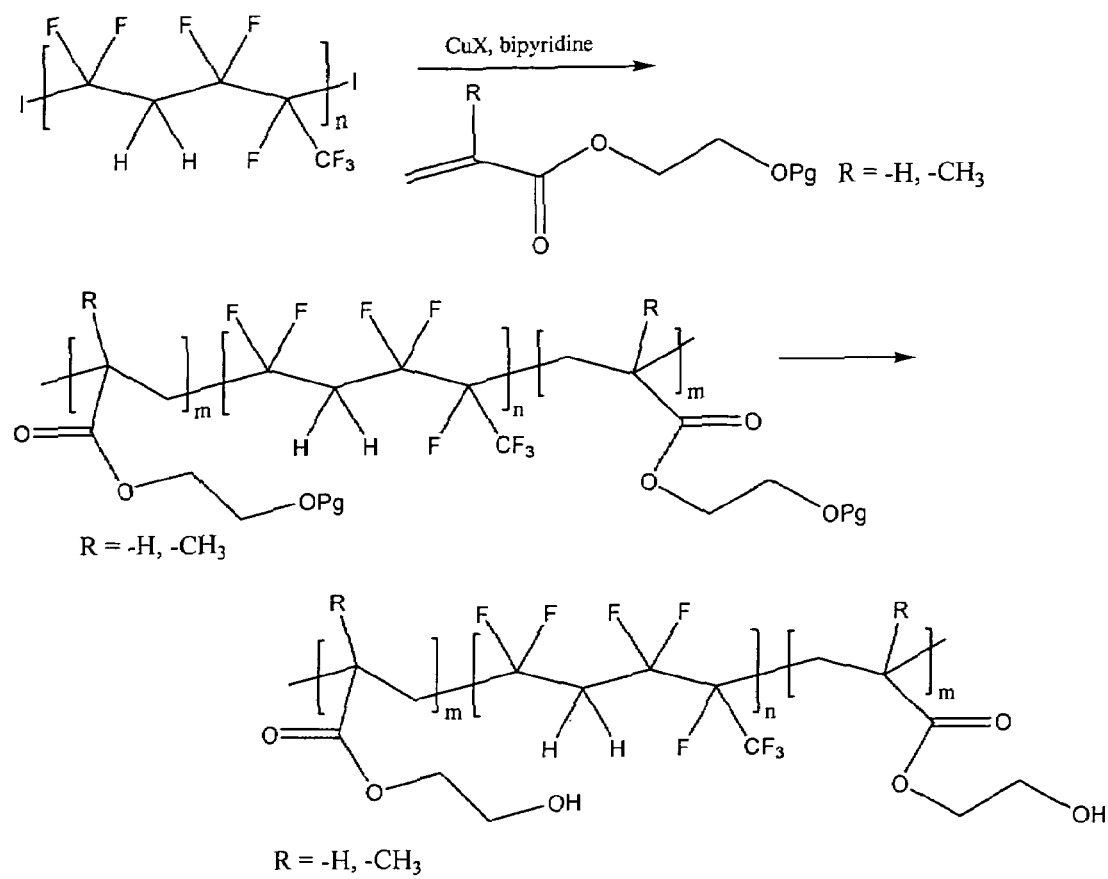
FIG. 1 is a scheme for making a block copolymer having non-fluorinated blocks bearing hydrophilic ethylene glycol pendent groups.

A block copolymer comprising a fluorinated block and a non-fluorinated block and method of making the block copolymer are provided. Also provided herein is a coating on an implantable device comprising the block copolymer and optionally a bioactive agent and method of using the implantable device.

Fluorinated Block Copolymer

A block of non-fluorinated polymer can be incorporated into a fluorinated polyolefin to form a block copolymer comprising a non-fluorinated block and a fluorinated block. The non-fluorinated block provides the polymer with improved vascular responses and/or improved permeability which are desirable for controlled release of a bioactive agent.

Fluorinated Blocks

In accordance with one aspect of the invention, the fluorinated block copolymer can be synthesized via a fluorinated macromer where at least one of the two termini of the macromer is functionalized. In one embodiment, the termini of the fluorinated macromer are functionalized with two halo groups which can be two of chloro, bromo, iodo or a combination thereof. For example, the two halo groups can be two iodo groups. The functionalized fluorinated macromer can be then be used as a macro-initiator to form a block copolymer with non-fluorinated monomers. The term fluorinated macromer refers to a poly(fluoroolefin). As used herein, the term poly(fluoroolefin) is used inter-exchangeably with the term poly(fluoroalkene).

In an embodiment, the di-halo fluorinated macromer can be a poly(fluorinated olefin) bearing two halogen groups at both termini. This dihalo fluorinated macromer can be readily synthesized by polymerizing a fluorinated olefin or a mixture of a fluorinated olefin in the presence of a dihalide and a peroxide (Ying, et al., Polym. Preprints 39(2):843 (1998); Zhang, et al., Polymer 40:1341 (1999); and Modena, et al., J. fluorine Chem. 4315(1989)). For example, a diiodo fluorinated macromer having as repeating unit —CF$_2$CH$_2$CF$_2$CF(CF$_3$)— can be readily synthesized by polymerizing a mixture of vinylidene fluoride and 1,1,2,3,3,3-hexafluoropropene in the presence of a peroxide and 1,2-diiodo-1,1,2,2-tetrafluoroehthane (Scheme 1) (Ying, et al., Polym. Preprints 39(2):843 (1998); Zhang, et al., Polymer 40:1341 (1999); and Modena, et al., J. fluorine Chem. 43 15 (1989)).

Scheme 1

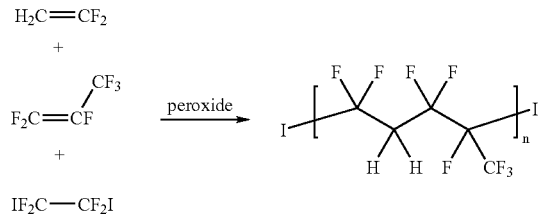

Non-fluorinated Blocks

Materials or polymers useful as the non-fluorinated blocks described herein include any polymers or macromers that can be directly attached to a fluorinated macromer described herein or polymers or macromers that can be functionalized to attach one or more functional groups such as hydroxyl, amino, halo, and carboxyl and other linking groups. Exemplary materials or polymers useful as the non-fluorinated blocks include, but are not limited to, polyolefins, polyalkylene oxides, polyglycols such as poly(ethylene glycol) and poly(propylene glycol), polylactic acid, poly(lactide-co-glycolide), polyhydroxyalkanoate, poly(hydroxybutyrate-co-valerate); polyorthoester; polyanhydride; poly(glycolic acid-co-trimethylene carbonate); polyphosphoester; polyphosphoester urethane; poly(amino acids); poly(cyanoacrylates); poly(trimethylene carbonate); poly(iminocarbonate); copoly(ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose acetate; cellulose butyrate; cellulose acetate butyrate; cellophane; cellulose nitrate; cellulose propionate; cellulose ethers; and carboxymethyl cellulose. As used herein, the term "non-fluorinated block" may include fluorinated pendant groups such as —CF$_3$.

In another embodiment, the non-fluorinated block can be incorporated into the fluorinated block by polymerizing an unsaturated compound, for example, acrylate or methacrylate using a catalyst such as a copper catalyst in the presence of a di-halo fluorinated macromer. For example, a block copolymer with a perfluorinated block can be made from monomers including vinylidene fluoride, hexafluoropropylene, tetrafluoroethylene, and other fluorinated olefins in the presence of a fluorinated dihalide under conditions of a standard radical polymerization (Ying et al., 1998; Zhang et al., 1999; and Modena et al., 1989, supra) to form a fluorinated di-halo macromer which can undergo polymerization with an unsaturated compound via an ATRP catalyst, as shown in Scheme 2 (Perrier, et al., Tetrahedron Lett 58 4053 (2002); Jo, et al., Polym Bull (Berlin) 44:1 (2002)).

Scheme 2

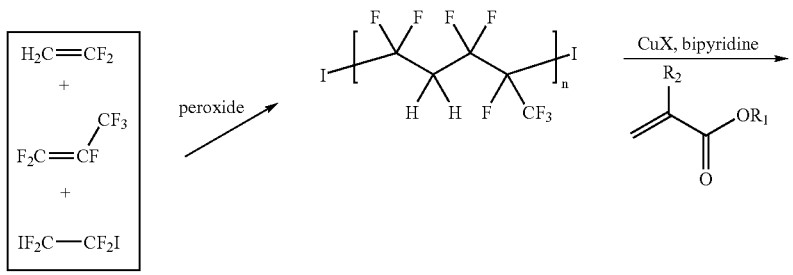

-continued

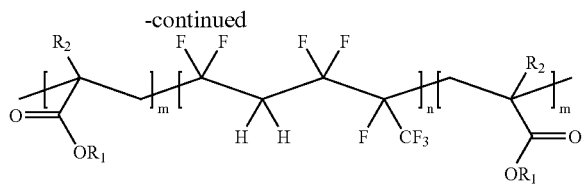

$R_1 =$ —$CH_3$, —$CH_2CH_2CH_2CH_3$, —$CH_2CH_2OH$, —$CH_2CH_2O$—$[CH_2CH_2O]_x$—H;
$R_2 =$ —H, —$CH_3$, —$CH_2CH_3$

The fluorinated di-halo macromer can be used to attach the macromer to many other types of polymers. For example, the di-halo groups can be replaced by many functional groups, for example, functional groups bearing a negative or partially negative charge. This allows the formation of a block copolymer bearing a poly(fluorinated olefin) block and one or two blocks of other nature such as polyesters, polyethers, polyanhydrides, polyglycols, poly(alkylene oxides), polyhydroxyalkanoates, polyphosphazenes, polyurethanes, or other biocompatible polymers commonly used in the art of drug delivery. The fluorinated di-halo macromer can form into a metallo macromer, which may be useful for linking the macromer with another biocompatible block or polymer.

As shown in Scheme 2, many different polymers can be made. For example, in addition to variations of the substituents such as $R_1$ and $R_2$ in Scheme 2, the ratio of the fluorinated block to the non-fluorinated block can be varied, leading to formation of block copolymers having different level of hydrophobicity and permeability with different surface and mechanical properties. For example, following the method shown in Scheme 2, block copolymers comprising a fluorinated block and non-fluorinated blocks of hydrophilic monomers such as hydroxyethyl methacrylate, hydroxypropyl methacrylate, N-vinyl pyrrolidone, or polyethylene glycol acrylate can be synthesized. The monomers with labile hydroxy functionalities can be protected with a protecting group (Pg), which can be cleaved at the completion of the reaction (FIG. 1). The protecting group can be, for example, t-butyl-dimethylsilane or trimethylsilane which can then be deprotected in stochiometric yields with acidic hydrolysis.

In one embodiment, the block copolymer described herein has a fluorinated block having the following structure:

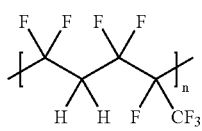

and a non-fluorinated block has the following structure:

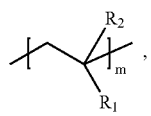

wherein $R_1$ can be —$CH_3$, —$CF_3$, —$CH_2CH_3$, —$CH_2CH_2CH_3$, —$CH_2CH_2CH_2CH_3$, -phenyl, naphthyl, —$COOR_3$, or —$CONR_3R_4$;

wherein $R_2$ can be —H, —$CH_3$, —$CF_3$, —$CH_2CH_3$, —$CH_2CH_2CH_3$, —$CH_2CH_2CH_2CH_3$, -phenyl, or naphthalenyl; and wherein $R_3$ and $R_4$ can be —$CH_3$, —$CH_2CH_3$, —$CH_2CH_2CH_3$, —$CH_2CH_2CH_2CH_3$, —$CH_2CH_2OH$, or -PEG.

In another embodiment, the block copolymer has a formula of the following structure:

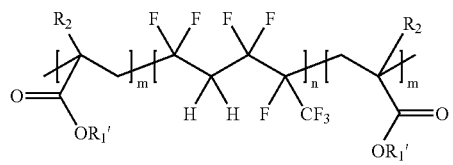

wherein $R_1'$ can be —$CH_3$, —$CH_2CH_3$, —$CH_2CH_2CH_3$, —$CH_2CH_2CH_2CH_3$, —$CH_2CH_2OH$, or -PEG, and wherein $R_2$ can be —H or —$CH_3$, —$CF_3$, —$CH_2CH_3$, —$CH_2CH_2CH_3$, —$CH_2CH_2CH_2CH_3$, -phenyl or naphthyl.

In a further embodiment, the block copolymer has a formula of the following structure:

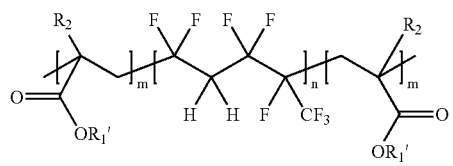

wherein $R_1'$ is —$CH_3$, —$CH_2CH_3$, —$CH_2CH_2CH_3$, —$CH_2CH_2CH_2CH_3$, —$CH_2CH_2OH$, or -PEG, and wherein $R_2$ is —H or —$CH_3$.

In still a further embodiment, the block copolymer described herein has a fluorinated block having the following structure:

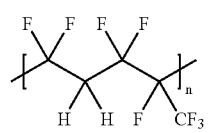

and a non-fluorinated block that can be polyesters, polyethers, polyanhydrides, polyglycols, poly(alkylene oxides), polyhydroxyalkanoates, polyphosphazenes, polyurethanes, or a combination thereof.

Compositions of Fluorinated Block Copolymers

The fluorinated block copolymer described above can be used to form coating compositions for coating an implantable device, for example, a stent. The fluorinated block copolymer can be used alone or in combination with another polymer. For use as DES coatings, the composition can include a bioactive agent.

Bioactive Agents

The bioactive agent can be any agent that is biologically active, for example, a therapeutic, prophylactic, or diagnostic agent. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Compounds with a wide range of molecular weight can be encapsulated, for example, between 100 and 500,000 grams or more per mole. Examples of suitable materials include proteins such as antibodies, receptor ligands, and enzymes, peptides such as adhesion peptides, saccharides and polysaccharides, synthetic organic or inorganic drugs, and nucleic acids. Examples of materials which can be encapsulated include enzymes, blood clotting factors, inhibitors or clot dissolving agents such as streptokinase and tissue plasminogen activator, antigens for immunization, hormones and growth factors, polysaccharides such as heparin, oligonucleotides such as antisense oligonucleotides and ribozymes and retroviral vectors for use in gene therapy. Representative diagnostic agents are agents detectable by x-ray, fluorescence, magnetic resonance imaging, radioactivity, ultrasound, computer tomography (CT) and positron emission tomography (PET). Ultrasound diagnostic agents are typically a gas such as air, oxygen or perfluorocarbons.

In the case of controlled release, a wide range of different bioactive agents can be incorporated into a controlled release device. These include hydrophobic, hydrophilic, and high molecular weight macromolecules such as proteins. The bioactive compound can be incorporated into polymeric coating in a percent loading of between 0.01% and 70% by weight, more preferably between 1% and 35%% by weight.

In one embodiment, the bioactive agent can be for inhibiting the activity of vascular smooth muscle cells. More specifically, the bioactive agent can be aimed at inhibiting abnormal or inappropriate migration and/or proliferation of smooth muscle cells for the inhibition of restenosis. For example, the bioactive agent can be for enhancing wound healing in a vascular site or improving the structural and elastic properties of the vascular site. Examples of active agents also include antiproliferative substances such as actinomycin D, or derivatives and analogs thereof (manufactured by Sigma-Aldrich 1001 West Saint Paul Avenue, Milwaukee, Wis. 53233, or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known as Everolimus, available from Novartis as Certican™), 40-O-(3-hydroxy)propyl-rapamycin, 40-O-[2-(2-hydroxy)ethoxy]ethyl-rapamycin, and 40-O-tetrazole-rapamycin. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent required to inhibit the desired cellular activity of the vascular region can depend upon factors such as the particular circumstances of the patient, the nature of the trauma, the nature of the therapy desired, the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Methods of Using the Coating Composition

The coating composition can be coated onto any implantable device by any established coating process, e.g., a spray process. Generally, the coating process involves dissolving or suspending the composition in a solvent to form a solution or a suspension of the coating composition, and then applying the solution or suspension to an implantable device such as a stent.

As used herein, an implantable device may be any suitable medical substrate that can be implanted in a human or veterinary patient. A exemplary implantable device is a stent such as DES. Examples of stents include self-expandable stents, balloon-expandable stents, and stent-grafts. Other exemplary implantable devices include grafts (e.g., aortic grafts), artificial heart valves, cerebrospinal fluid shunts, pacemaker electrodes, and endocardial leads (e.g., FINE-LINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

The implantable device described herein can be used to treat any medical condition, for example, a vascular disorder in an animal such as a human. Representative medical conditions that can be treated using the implantable device described herein include, but are not limited to, cancer, restenosis, vulnerable plaque, thrombosis or inflammation.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. An implantable device comprising a coating which comprises a block copolymer, the block copolymer comprising a fluorinated block and at least one non-fluorinated block, wherein the fluorinated block is a poly(fluoroalkene), and
    wherein the fluorinated block has repeating units of the following structure:

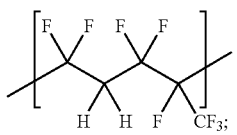

wherein the non-fluorinated block has repeating units of the following structure:

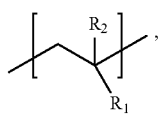

wherein $R_1$ is selected from the group consisting of —$CH_3$, —$CF_3$, —$CH_2CH_3$, —$CH_2CH_2CH_3$, —$CH_2CH_2CH_2CH_3$, -phenyl, naphthyl, —$COOR_3$, and —$CONR_3R_4$;
    wherein $R_2$ is selected from the group consisting of —H, —$CH_3$, —$CF_3$, —$CH_2CH_3$, —$CH_2CH_2CH_3$, —$CH_2CH_2CH_2CH_3$, -phenyl, and naphthyl; and
    wherein $R_3$ and $R_4$ are selected from the group consisting of —$CH_3$, —$CH_2CH_3$, —$CH_2CH_2CH_3$, —$CH_2CH_2CH_2CH_3$, —$CH_2CH_2OH$, and -PEG.

2. The implantable device of claim 1, wherein the block copolymer has a formula comprising three blocks, the middle block having repeating units of the following structure:

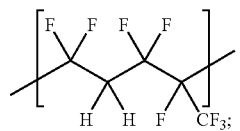

and the two end blocks having repeating units of the following structure

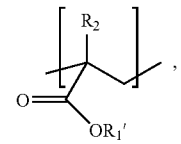

wherein $R_1'$ is selected from the group consisting of —$CH_3$, —$CH_2CH_3$, —$CH_2CH_2CH_3$, —$CH_2CH_2CH_2CH_3$, —$CH_2CH_2OH$, and -PEG, and
    wherein $R_2$ is selected from the group consisting of —H or —$CH_3$, —$CF_3$, —$CH_2CH_3$, —$CH_2CH_2CH_3$, —$CH_2CH_2CH_2CH_3$, -phenyl and naphthyl.

3. The implantable device of claim 2 wherein $R_1'$ is selected from the group consisting of —$CH_3$, —$CH_2CH_3$, —$CH_2CH_2CH_3$, —$CH_2CH_2CH_2CH_3$, —$CH_2CH_2OH$, or -PEG, and
    wherein $R_2$ is —H or —$CH_3$.

4. The implantable device of claim 3, which is a drug-eluting stent, wherein the coating further comprises a bioactive agent.

5. The implantable device of claim 4, wherein the bioactive agent is selected from the group consisting of tacrolimus, dexamethasone, rapamycin, everolimus, 40-O-(3-hydroxy)propyl-rapamycin, 40-O-[2-(2-hydroxy)ethoxy]ethyl-rapamycin, and 40-O-tetrazole-rapamycin.

6. The implantable device of claim 2, which is a drug-eluting stent, wherein the coating further comprises a bioactive agent.

7. The implantable device of claim 6, wherein the bioactive agent is selected from the group consisting of tacrolimus, dexamethasone, rapamycin, everolimus, 40-O-(3-hydroxy)propyl-rapamycin, 40-O-[2-(2-hydroxy)ethoxy]ethyl-rapamycin, and 40-O-tetrazole-rapamycin.

8. A method of treating restenosis or vulnerable plaque, comprising implanting in a human being in need thereof the implantable device of claim 7.

9. The implantable device of claim 1, which is a drug-eluting stent, wherein the coating further comprises a bioactive agent.

10. The implantable device of claim 9, wherein the bioactive agent is selected from the group consisting of tacrolimus, dexamethasone, rapamycin, everolimus, 40-O-(3-hydroxy)propyl-rapamycin, 40-O-[2-(2-hydroxy)ethoxy]ethyl-rapamycin, and 40-O-tetrazole-rapamycin.

11. A method of treating restenosis or vulnerable plaque, comprising implanting in a human being in need thereof the implantable device of claim 10.

12. A method of treating restenosis or vulnerable plaque, comprising implanting in a human being in need thereof the implantable device of claim 1.

13. An implantable device comprising a coating which comprises a block copolymer, the block copolymer comprising a fluorinated block and at least one non-fluorinated block, wherein the fluorinated block is a poly(fluoroalkene), wherein the fluorinated block has repeating units of the following structure:

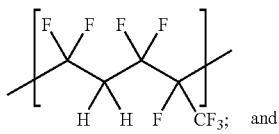

and wherein the non-fluorinated block is a polymer selected from the group consisting of polyesters, polyethers, polyanhydrides, polyglycols, poly(alkylene oxides), polyhydroxyalkanoates, polyphosphazenes, polyurethanes, and a combination thereof.

14. The implantable device of claim 13, which is a drug-eluting stent, wherein the coating further comprises a bioactive agent.

15. The implantable device of claim 14, wherein the bioactive agent is selected from the group consisting of tacrolimus, dexamethasone, rapamycin, everolimus, 40-O-(3-hydroxy)propyl-rapamycin, 40-O-[2-(2-hydroxy)ethoxy]ethyl-rapamycin, and 40-O-tetrazole-rapamycin.

16. An implantable device comprising a coating which comprises a block copolymer, the block copolymer comprising a fluorinated block and at least one non-fluorinated block, wherein the fluorinated block is a poly(fluoroalkene) wherein the device is a drug-eluting stent, and wherein the coating further comprises a bioactive agent.

17. The implantable device of claim 16, wherein the bioactive agent is selected from the group consisting of tacrolimus, dexamethasone, rapamycin, everolimus, 40-O-(3-hydroxy)propyl-rapamycin, 40-O-[2-(2-hydroxy)ethoxy]ethyl-rapamycin, and 40-O-tetrazole-repamycin.

18. A method of treating restenosis or vulnerable plaque, comprising implanting in a human being in need thereof the implantable device of claim 17.

* * * * *